United States Patent [19]

Melmon et al.

[11] Patent Number: 4,996,221

[45] Date of Patent: Feb. 26, 1991

[54] HISTAMINE DERIVATIVES AS IMMUNE MODULATORS

[75] Inventors: Kenneth L. Melmon, Woodside; Murray Goodman, La Jolla; Manzoor M. Khan, San Carlos; Debra Marr-Leisy, Los Alamitos; Michael Verlander, Rancho Palos Verdes, all of Calif.

[73] Assignee: The Board of Trustees of the Leland Stanford Junior University, Stanford, Calif.

[21] Appl. No.: 2,781

[22] Filed: Jan. 13, 1987

[51] Int. Cl.$^5$ .................. A61K 31/415; C07D 233/64
[52] U.S. Cl. .................... 514/399; 548/342; 548/344; 514/19; 514/398; 530/807
[58] Field of Search ............ 548/342, 344; 260/998.2; 514/396, 398, 399, 19; 435/68; 530/807

[56] References Cited

U.S. PATENT DOCUMENTS

| | | |
|---|---|---|
| 2,988,478 | 6/1961 | Gordon .................... 514/398 |
| 4,333,946 | 6/1982 | Durant et al. ............. 548/342 |
| 4,340,598 | 7/1982 | Furukawa et al. .......... 548/342 |
| 4,532,331 | 7/1985 | Frazee et al. ............. 548/342 |
| 4,687,873 | 8/1987 | Goodman et al. .......... 560/28 |
| 4,837,305 | 1/1987 | Goodman et al. .......... 530/345 |

FOREIGN PATENT DOCUMENTS

| | | | |
|---|---|---|---|
| 889706 | 2/1962 | European Pat. Off. ............ 514/398 |
| 0010418 | 4/1980 | European Pat. Off. ............ 514/398 |
| 0208953 | 1/1987 | European Pat. Off. ............ 435/68 |
| 2454795 | 5/1975 | Fed. Rep. of Germany ...... 548/342 |
| 8602620 | 10/1986 | South Africa . | |

OTHER PUBLICATIONS

Khan, Journal of Immunology, vol. 137, No. 1, 1986, pp. 308–314.
Khan et al, The Journal of Immunology, vol. 134, No. 6, (6/1985), pp. 4100–4106.
Piptide Hormones, 6/1976, Rudinger et al, pp. 1–7.

*Primary Examiner*—Johnnie R. Brown
*Assistant Examiner*—T. Wessendorf
*Attorney, Agent, or Firm*—Richard L. Neeley

[57] ABSTRACT

Histamine derivatives are disclosed which find use as effect and tissue-specific immune modulators. Specifically, the primary terminal nitrogen in histamine is derivatized to introduce a variable length side chain having 0 to 1 branch of from 1 to 3 carbons; 0 to 2 non-oxo-carbonyl groups; 0 to 4 heteroatoms, other than the non-oxo carbonyl oxygen; 0 to 1 aryl or alkylaryl group; and 0 to 1 functionally bound amino acid, polypeptide, or protein or derivative thereof.

16 Claims, No Drawings ns that are effect or cell specific.
HISTAMINE DERIVATIVES AS IMMUNE MODULATORS This work was supported in part under NIH grant NHLBI R0126340. Accordingly, the government has certain rights to this invention.

BACKGROUND OF THE INVENTION

1. Field of the Invention

With the increased level of understanding concerning the immune response process in mammals, there is a growing awareness that certain molecules play a significant role in immune modulation. Unfortunately, these molecules are generally nonspecific as to their effects on single cell types in a mixture of cells. A critical need exists for agonists that are effect or cell specific.

Histamine is a small molecule that has been shown to have a significant role in the immune response process in mammals. However, its ubiquitous effects on many cells that have receptors for histamine limits its possible immunotherapeutic use. Histamine derivatives that are tissue directed or effect specific would significantly aid in determining the role of histamine in immune modulation and produce valuable immunotherapeutics.

Histamine can substantially modulate models of immune responses in mammals, particularly models of delayed hypersensitivity and T and B cell functions. Histamine is synthesized during different phases of response to antigen and is able directly or indirectly to effect further responses to antigen. It is possible that the concentration of histamine in tissue during inflammation and immune response can modify the function of a number of lymphoid cells. Although these effects may be substantial, the direct effects on single cell types in a mixture of cells cannot be determined unless the agonists are effect or cell specific. Ubiquitous effects of agonists on all cells that have receptors for histamine would limit any immunotherapeutic use of histamine. See Khan, et al., *Clin.Immunol. Rev.* (1985) 4:1 Melmon, et al., *Am. J. Med.* (1981) 71:100: and Rocklin et al., *Cell Immunol.* (1978) 37:162.

Histamine is an autacoid as are catecholamines, prostaglandins and some peptides, e.g., bradykinin and probably lymphokines. Autacoids differ from hormones in that they are made at their local sites of action and they can be made in a variety of tissues. Autacoids play an important role in mediating inflammation. During inflammation, certain events may occur which include: protein denaturation, lowering of local pH, release of "new peptides" and lysosomal enzymes, and the like. Such events create a setting in which the immune system should not overreact to the new products. Yet, despite the ability of inflammation to generate likely immunogens, the inflammatory process usually is not accompanied or followed by grossly abnormal immune responses. Autacoids appear to somehow modulate this response.

Autacoids affect natural suppressor cells, T cell subsets, and B cells during various stages of immunity. Receptors for autacoids are non-randomly distributed (in number and affinity for agonist) on cells that carry out immune functions. Precursor B cells do not appear to have histamine and catecholamine receptors, while B cells committed to produce antibodies do. T suppressor ($T_s$ cells modulate the cAMP responses of T helper ($T_h$) and T cytolytic ($T_c$) cells to histamine. Mitogens alter responsiveness of these cells to histamine. Some lymphocytes that respond to histamine have both $H_1$ and $H_2$ receptors on them while others only have $H_2$ receptors. In some lymphocytes the $H_2$ receptors seem to modify the responses to $H_1$ agonism: in others there is no such interplay. In some cells biologic response is inhibitory (e.g., reduced release of antibody from B cells: inhibition of lymphokine release or lysis of target cells by T effector cells and inhibition of release of histamine from mast cells): in others the response enhances immune function (e.g., enhanced suppression by natural suppressor and $T_s$ cells or $T_h$ cell proliferation). The autacoids seem to be enhancing selected early events in immune response (e.g., enhanced suppressor function) while inhibiting later phases of phenotypic manifestations (e.g., release of lymphokines or antibodies) of immunity.

The appearance of naturally occurring suppressor cells in the spleens of neonatal or irradiated mice may have a key role in induction of immune tolerance. See, Strober et al., *Ann. Rev. Immunol.* (1984) 2:219: Hertel-Wulff et al., *J. Immunol.* (1984) 133:2791: Okada et al., *J. Expt. Med.* (1982) 156:522: and Okada et al., *J. Immunol.* (1982) 129:1892. These cells are related to NK cells in terms of their surface phenotype but differ in function. The natural suppressor cells appear briefly during the early maturation of lymphoid tissue but can be induced in adults by total lymphoid irradiation. The cells have the unique feature of inhibiting the antigen-specific cytolytic arm of alloreactive immune response but leave the antigen-specific suppressive arm intact. In this way, alloreactions in the regulatory milieu of natural suppressor (NS) cells generate large numbers of antigen-specific suppressor cells that in turn maintain tolerance in vivo. Thus, the natural suppressor cells may play an important role in preventing the development of host versus graft and graft versus host diseases in allogeneic bone marrow chimeras, and in immune tolerances in the neonatal and total lymphoid irradiated (TLI) mice.

Histamine activates human $T_s$ cells and enhances the suppressive ability of murine NS cells in vitro. See, Khan et al., *J. Immunol.* (1985) 134:4100 and Sansoni et al., *J. Clin. Invest.* (1985) 75:650. After pretreatment of human $T_s$ cells (Leu-2., 9.3 ) with histamine, both phytohemagglutinin-induced $T_h$ cell proliferation and pokeweed mitogen-induced B cell differentiation were inhibited. The effects were mediated via $H_2$ receptors. The enhancement of natural suppressor function is via $H_1$ receptors. Natural suppressor cells can be propagated and cloned in long-term tissue culture and cause nonspecific suppression in both in vitro and in vivo models of mixed leukocyte reactions. Therefore, it is important to develop histamine derivatives which can affect the ability of NS cells to modulate graft versus host reaction in vivo.

2. Brief Description of the Relevant Art

Strategies have been developed for derivatizing catecholamines that are relevant to the subject invention, the relevant parts of which are herein incorporated by reference. See, Rosenkranz et al., *Mol. Pharmacol.* (1983) 24:429: Jacobson et al., *Intl. J. Pept. Protein Res.* (1983) 22:284: Verlander et al., *Biopolymers* (1983) 22:531: Rosenkranz et al., *J. Pharmacol. Exp. Ther.* (1983) 227:267: Jacobson et al., *J. Med. Chem.* ( 983) 26:492: and U.S. Pat. No. 4,337,207.

SUMMARY OF THE INVENTION

Derivatives of histamine are provided which demonstrate a selectivity in mammals as to the type of cell to which they bind and as to the degree of the effect they exert upon the target cell. The type of side chain attached to the parent histamine regulates the cell type to which the derivative binds and exercises its effect and the degree to which that effect is modulated. The subject compounds avoid the problem of histamine's pleiotropic effects which are due to ubiquitous binding to many varied cells, while still retaining specific desirable histamine effects on cellular behavior.

The subject compounds have a histamine ring structure derivatized at the terminal nitrogen to introduce a variable length chain having 0 to 1 branch of from 1 to 3 carbon atoms: 0 to 2 non-oxo-carbonyl groups: 0 to 4 heteroatoms, other than the non-oxo-carbonyl oxygen: 0 to 1 aryl or alkaryl group: and 0 to 1 amino acid, polypeptide, or protein or derivative thereof, bound through the chain to the histamine ring. Such derivatives find use as immunomodulators that are effect and tissue specific.

DESCRIPTION OF THE SPECIFIC EMBODIMENTS

The present invention relates to derivatives of histamine which can modulate the immunological response in mammals while avoiding the pleiotropic effects of histamine on both cells that mediate immunity and tissue unrelated to immunity. These derivatives of histamine interact with specific receptors and can be directed at subsets of cells and away from other tissues such as the cardiovascular tissues.

The subject histamine derivatives are modified at the histamine side chain primary amine by derivatizing with an aliphatic, e.g., alkyl, or aralkyl (aryl group bound to an aliphatic chain) where the aliphatic chain may be branched or unbranched of variable length, which may include oxo-carbonyl, e.g., keto, non-oxo-carbonyl groups, e.g., carboxamide or heteroatoms. These modified histamine agonists may be further modified by linkage to carrier molecules such as amino acids, polypeptides, proteins, or derivatives thereof.

Generally, the subject histamine derivatives and pharmacologically acceptable salts thereof are formed by derivatizin the primary amine in histamine to introduce a variable length side chain having 0 to 1 branch of from 1 to 3 carbons, preferably methyl, particularly alpha to the amino group: 0 to 2 non-oxo-carbonyl groups: 0 to 4 heteroatoms, other than the non-oxo carbonyl oxygen: 0 to 1 aryl or substituted aryl group, preferably the substituent being methyl or trifluoromethyl located para to the histamine linking chain: and 0 to 1 covalently bonded amino acid, polypeptide, protein, or derivative thereof.

Specifically, the subject biologically active derivatives of histamine have the formula:

His—NH—(X)—(CH$_2$)$_n$—(Y) (HA)$_b$ wherein:

His—NH intends the histaminyl residue, with the NH being the side chain amino (2-(4'-imidazolinyl)ethylamino):

n indicates the number of methylene groups in the chain and is usually 0 to 10, more usually 2 to 6, and preferably 2 to 5:

X is a carbonyl, a methylene, or alkylidene, i.e., —CHR—, where R is an alkyl chain of from 1 to 3 carbons, preferably methyl:

Y is a terminal group, either a methyl or amide, i.e., —CONHZ, wherein Z is hydrogen or preferably Z is an organic group, thereby producing an N-substituted amide, where the N-substituent is an alkyl group, particularly a straight chain, i.e., —(CH$_2$)m—CH$_3$, wherein m is usually from 0 to 10, more usually 2 to 6, and preferably 2 to 5: an aryl or substituted aryl group, i.e.,

where phi is phenylene, particularly para-phenylene, D is hydrogen, methyl or heteroatom-substituted methyl, preferably halomethyl, more particularly trifluoromethyl, and the D group is para to the chain: or an amino acid, polypeptide, protein, or derivative thereof:

A is a physiologically acceptable counterion such as acetate, chloride, sulfate, phosphate, and the like, preferably chloride: and b indicates the number of additional protons and counterions found in the salt (e.g., the number of basic amines avalable for neutralization) and is usually 0 to 2, preferably from 1 to 2, with the proviso that when Y is an amino acid, polypeptide, protein, or derivative thereof, b may be greater than 2 to neutralize partially or totally any additional charge introduced by Y. Further, when Y is methyl and either X is carbonyl or R is methyl. n is other than 4.

Histamine derivatives of particular interest include compounds of the formulas:

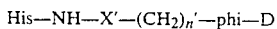

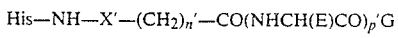

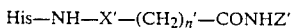

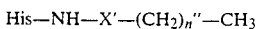

wherein:

His—NH is the histaminyl residue, with the NH being the side chain amino:

X' is CO, CH$_2$, or CHCH$_3$;

phi is phenylene, particularly para-phenylene:

D is methyl or trifluoromethyl:

E is any naturally occurring (especially genetically encoded) amino acid residue side chain: i.e., E is H (in which case the amino acid is glycine) or a side chain of an amino acid bonded to the alphacarbon of glycine (in which case the amino acid is an amino acid other than glycine):

G is OH, NH$_2$ or NHCH$_3$;

Z' with the nitrogen to which it is attached is a poly(amino acid):

n' is an integer of from 2 to 5, usually 3 to 5;

n" is an integer of from 2 to 3;

p' is an integer of from 1 to 8.

More specifically, individual histamine derivatives of interest come within the structure:

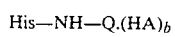

wherein A and b are as defined above and Q is defined as:

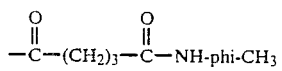

-continued

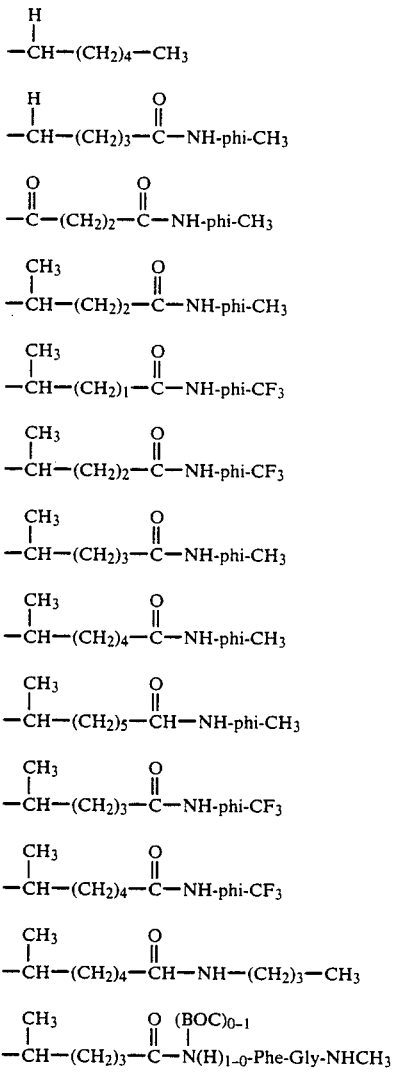

where BOC is the t-butyloxycarbonyl blocking group.

The histamine derivatives may be synthesized by various methods according to procedures well known in the art. The acylated derivatives may be prepared from histamine and the appropriate carboxylic acid via the mixed anhydride, carbodiimide or aryl halide method. Unbranched alkylated derivatives may be synthesized either by a displacement reaction using a halide or pseudohalide compound, e.g., bromo, chloro, tosyl, etc. or, preferably, by reductive amination of histamine with an aldehyde in the presence of sodium cyanoborohydride or similar agent. Branched, alkylated derivatives may be prepared by reductive amination of histamine with the appropriate methyl ketone derivative or by halide or pseudohalide displacement (using conditions that favor displacement over elimination). Although these are possible synthesis routes, other methods well known in the art are contemplated as also producing compounds of the subject invention.

The histamine derivatives may be purified by conventional purification techniques, such as crystallization, or by chromatographic techniques, such as column chromatography, high performance liquid chromatography, preparative thin-layer chromotography. or the like.

It is understood that the subject invention includes derivatives of histamine wherein histamine is connected by a linking group to an amino acid or poly(amino acid) molecule thereby defining a conjugate. The histamine derivative may be linked to a carrier such as polypeptides, proteins, glycoproteins or derivatives thereof (all included within the name poly(amino acid).

The conjugates may serve a variety of functions, changing the physiological character of the histamine derivative, acting as immunogens, providing for cell specific binding and the like. Depending on the purpose of the conjugate, the nature of the histamine derivative may be modified to lesser or greater degrees by adding additional functionalities, substituting groups or the like. Particularly for the production of antibodies from immunogens, a group may be substituted for another group, e.g., methyl or trifluoromethyl with carboxyl. Also, in the case of immunogens, substitution at histamine or intermediate the ends of the histamine derivative may be desirable.

The conjugates may be bonded through a wide variety of functionalities to form amides, methyleneamine, thioether, disulfide, sulfonamide, azo, amidine, etc. The particular functionality chosen will depend upon the purpose of the conjugate, ease of synthesis, stability of the linking functionality, affect of the linking group on the physical, chemical like.

For the most part, the conjugates of this invention will have the following formulas:

wherein all of the symbols have been defined previously except that a hydrogen, methyl or trifluoromethyl group may be replaced by W, which is a bond or linking group to T. wherein T is an amino acid derivative or poly(amino acid), and d is the number of histamine derivatives per T, usually being on the average in the range of 1 to 50, more usually 1 to 20, and frequently 1 to 10:

W is a bond or linking group of at least one atom other than hydrogen and may be methylene, e.g., by reductive amination of a periodate cleaved sugar or other aldehyde, non-oxo-carbonyl, thio, alkylene-non-oxo-carbonyl, alkylene, alkylenethio, arylene-non-oxo-carbonyl, arylazo, etc., the particular linking group not being critical except as indicated herein:

T is an amino acid or poly(amino acid) of from about 2 to 2000, usually about 2 to 1000, amino acid residues, which may also include sugars or lipids, and may be a carrier for antibody formation, e.g., bovine serum albumin, keyhole limpet hemocyanin, $\beta$-globin, etc., a poly(amino acid) usually of at least about 100 amino acids, or for site specific binding, may be a hormone, lymphokine, growth factor, or the like The linking group may provide for linkage which is resistant or susceptible to hydrolytic cleavage under physiological conditions.

The functionalities bonded to the histamine derivative and carrier are selected so as to complement one another in such a way as to allow the formation of a suitable chemical bond between the two. Thus, if the carrier contains an amine functional group, e.g., lysine or p-aminophenylalanine side chains, the functionality of the histamine derivative may be a carboxylic acid, a sulfonic acid, etc.

The number of histamine derivatives per carrier may be one, or any number greater than one. The number of histamine derivatives per carrier molecule is dependent upon the number of appropriate functional groups in the carrier and the stoichiometry used during the coupling reaction.

Synthesis routes are well known in the art. One method would involve the preparation of appropriate histamine derivatives where the extended amine side chain or other location on histamine has a suitable functional group. One or more functionalized histamine derivatives are then, in turn, coupled to appropriate side chains of the carrier. Alternatively, a method of synthesis may involve the initial modification of the carrier by coupling the derivative group moiety containing a further functional group reactive with histamine directly to the carrier side chain. The resulting carrier derivative is then coupled directly to the histamine, for example, by a reductive amination reaction to produce the conjugate.

The reaction scheme should be selected, when appropriate, so that the desired physiological properties of the carrier are not detrimentally affected. This is particularly true with naturally-occurring carriers, such as hormones, lymphokines and proteins (including antibodies). Care should be taken not to denature the carrier or inactivate the antibody binding site during the linking reaction. The carrier should maintain at least a portion of its activity upon isolation.

It is understood that, in the manner of the previously described subject histamine derivatives, the conjugates may exist as various possible physiologically acceptable salts. Such salts may include counterions such as acetate, chloride, sulfate, phosphate, and the like.

Such modified and conjugated histamine derivatives may exhibit biological activity in terms of being selective modulators of immunity. One preferred use for such activity is to modulate the physiological activity on natural suppressor (NS) cells. Some histamine compounds show selective effects on NS cells, in that they are inactive on myocardial tissue, while other histamine compounds are selectively active on the myocardium. Some compounds augment the suppressive capacity of NS cells in a mixed leukocyte reaction (MLR).

The NS cells are present before antigenic challenge and lack antigen specificity. They may have a key role in induction of immune tolerance. These cells have the unique ability to inhibit the antigen-specific cytolytic arm of the alloreactive immune response but leave the antigen-specific suppressive arm intact. Massed cells play an interactive role with NS and also can independently contribute to immune suppression.

The subject compounds may be employed selectively to modulate an immune response of a mammal by introducing into the mammal an amount of the subject compound sufficient selectively to stimulate an immune response. The compound may be introduced into the vertebrate, usually mammal, in a physiologically acceptable carrier. The manner of application may be varied widely in accordance with methods well known in the art, which include but are not limited to: orally, parenterally, by injection or the like. Such factors as dosage levels, appropriate carrier and the like will vary depending upon the route of administration, type and size of host, and similar considerations. Concentrations and dosages will vary widely depending upon the purpose, host and particular derivative employed. Concentrations may vary from $10^{-1}$ to $10^{-5}$ M of the active component.

The following examples are offered by way of illustration and not by way of limitation.

EXPERIMENTAL

The following abbreviations are employed and are well-known in the art:
CAS : concanavalin A supernatant from rat spleen
MLR : mixed leukocyte reaction
NS : natural suppressor cells
TLI : total lymphoid irradiation
FCS : fetal calf serum
IBMX: isobutylmethylxanthine
PBS : phosphate buffered saline
TCA : trichloroacetic acid
ED : effective dosage Specific compounds are identified in some cases by two different reference numbers: e.g., (245) and (3). Underlined reference numbers are primarily used in the discussion of synthetic techniques while the smaller reference numbers (1—13) that are not underlined are used primarily in biological activity experiments. A list of both reference numbers and structures is set forth in Table 1.

EXAMPLE I Synthesis of Typical Histamine Derivatives

The histamine derivatives were synthesized by a variety of methods as exemplified below and were isolated either as the free base or the dihydrochloride salt. With the exception of compounds 245 and 266 (see Tables 1 and 2), the free bases were converted to their dihydrochloride salts by lyophilization from 0.1 N HCl before being submitted for biological assay. Compounds and 266 were assayed as the free base. Reaction conditions and yields for the reductive amination reaction of histamine and methyl ketones are given in Table 1. Elemental analyses are given in Table 2.

1-[2'-(4''-Imidazo)ethylamino]hexane,Dihydrochloride (248) (1)

Histamine dihydrochloride (0.50 g, 2.7 mmol) and n-hexanal (0.33 ml, 2.7 mmol) were dissolved in 10 ml of MeOH in a flask which had been flushed with nitrogen. Molecular sieves (3Å) were added and the mixture was stirred at room temperature for 40 minutes before addition of sodium cyanoborohydride (0.17 g, 2.7 mmol). After 10 hours, the MeOH was removed under reduced pressure, the residue dissolved in 75 ml 0.1 N HCl and extracted with CHCl$_3$ to remove unreacted aldehyde and the alcohol side product. The aqueous phase was made basic with saturated NaHCO$_3$ and extracted with n-BuOH The BuOH extracts were combined, washed with brine and the BuOH removed in vacuo. The residual material was triturated with isopropanol to separate the product from contaminating NaCl. The supernatant was concentrated under reduced pressure to an oil which was dissolved in CHCl$_3$, dried over Na$_2$CO$_3$ and acidified by the addition of 4N HCl in dioxane. The solvents were removed under reduced pressure to give 0.11 g (16%) of white solid. Recrystallization from EtOH gave a first crop of 31 mg of white crystals shown to be homogeneous by thin layer chromatography (BuOH:pyridine:AcOH:H$_2$O, 30:10:3:12, R$_f$=0.49), mp 229°–231° C.

5-[2'-(4''-Imidazo)ethylamino]pentanoic Acid p-Toluide, Dihydrochloride (249) (5)

The reactant 5-chlorovaleryl chloride (7.75 g. 0.05 mol) was dissolved in 50 ml dry THF and the solution cooled in an ice bath. p-Toluidine (5.35 g, 0.05 mol) and triethylamine (7.7 ml, 0.06 mol) were dissolved in 50 ml dry THF and the mixture added dropwise to the solution of acid chloride over a period of 1 hour. After the addition was complete, the solution was warmed to room temperature and stirred for an additional 3 hours. The THF was then removed under reduced pressure and the residue dissolved in 300 ml EtOAc. The EtOAc solution was extracted with $H_2O$, 0.5 N HCl, 2.5% NaCH, and brine, then dried over $Na_2SO_4$. After filtration and concentration of the filtrate under reduced pressure, hexane was added to induce crystallization. The product was isolated as white platelets (9.52 g, 78%) and was shown to be homogeneous by thin layer chromatography ($CHCl_3$:MeOH AcOH, 95:5:3, $R_f$TM 0.62), mp 92-93° C.

A 10 ml round-bottom flask equipped with condenser and nitrogen bubbler was flushed with nitrogen. 5-Chlorovaleric acid p-toluide (0.44 g, 1.9 mmol) and histamine free base (0.50 g, 4.5 mmole were dissolved in 2 ml dry n-propanol. The mixture was heated to 100° C. in an oil bath for 5 hours. After cooling to room temperature, the reaction mixture was dissolved in 100 ml 0.1 N HCl and extracted with $CHCl_3$. The aqueous layer was saturated with solid $NaHCO_3$, the pH brought to 9 by the addition of 1 N NaOH and the solution extracted with $CHCl_3$ and n-BuOH. The combined BuOH fractions were back-extracted with brine and the BuOH removed in vacuo. The white solid residue was triturated with BuOH to isolate the product from contaminating NaCl and the supernatant concentrated in vacuo to an oil. Lyophilization of the oil from $H_2O$ gave 0.20 g (35%) of compound 249 judged to be pure by thin layer chromatography (BuOH:pyridine:AcOH:H20, 30:10:3:12, $R_f$ =0 45). The product was converted to the hydrochloride chloride salt by treatment of a $CHCl_3$ solution of the product with 4 N HCl in dioxane. Removal of the solvents under reduced pressure followed by crystallization of the residue from EtOH/ether gave material shown to be pure by thin layer chromatography (same system and $R_f$ as given above), mp 225-227° C.

N-Hexamido-4-[2'-aminoethyl]imidazole (245) (3)

Caproic acid (0.11 g, 1.0 mmol) was dissolved in 5 ml dry THF and the solution cooled in an ice bath. N-Methylmorpholine (0.33 ml, 3.0 mmol) was followed by isobutylchloroformate (0.13 ml, 1.0 mmol) and the solution stirred for 10 minutes. Histamine dihydrochloride (0.18 g, 1.0 mmol) was dissolved in 1.0 ml DMP and added to the above solution. After allowing the reaction to warm to room temperature and stir overnight, the solvent was removed in vacuo and the residue dissolved in 0.1 N HCl (30 ml). The acidic solution was extracted with $CHCl_3$ and then saturated with solid $NaHCO_3$. The basic aqueous phase was then extracted with $CHCl_3$. The $CHCl_3$ phases were combined, washed with brine and dried over $Na_2SO_4$. Filtration to remove drying agent followed by removal of the solvent under reduced pressure gave a solid which was triturated with EtOH and dried to give 0.10 g (47%) of compound 245. The product was shown as a single spot on thin layer chromatography (BuOH:pyridine:AcOH:$H_2O$, 30:10:3:12, $R_f$=0.59), mp 128°-129° C.

5-[2'-(4''-Imidazo)ethylamido]glutaryl p-Toluidine (247) (4)

Glutaric anhydride (5.0 g, 44 mmol) was added to a solution of p-toluidine (9.39 g, 88 mmol) in dry THF. The clear brown solution immediately became warm and white crystals precipitated from the solution. The mixture was stirred at room temperature overnight followed by removal of the solvent under reduced pressure. The solid residue was dissolved in 120 ml 0.5 N NaOH and extracted with $CHCl_3$. Upon acidification of the aqueous layer with 3 N HCl (to pH (1), copious amounts of precipitate formed. The solid was isolated by filtration, washed extensively with $H_2O$, EtOAc, and ether and dried in vacuo to give 7.6 g of product. An additional 2 g of material was isolated by extraction of the initial acidic filtrate with EtOAc. The two crops of product were combined and recrystallized from MeOH/EtOAc to give 8.4 g (87%) of colorless needles shown to be homogeneous by thin layer chromatography ($CHCl_3$:MeOH:AcOH, 95:5:3, $R_f$=0.23), mp 176°-177.5° C.

The product (0.22 g, 1.0 mmol) and N-methylmorpholine (0.11 ml, 1.0 mmol) were dissolved in 5 ml dry DMF, the solution cooled to 0° C. and isobutyl chloroformate (0.13 ml, 1.0 mmol) added. After 10 minutes, a solution of histamine dihydrochloride (0.20 g, 1.1 mmol) and N-methylmorpholine (0.24 ml, 2.2 mmol) in 2 ml DMF was added. The reaction mixture was warmed to room temperature and stirred overnight. After removal of DMF in vacuo, the residue was dissolved in 40 ml 0.1 N HCl and extracted with $CHCl_3$ to remove unreacted starting acid. The aqueous phase was made basic by the addition of solid $NaHCO_3$ which induced the product to crystallize from the solution. The product was isolated by filtration, washed with $H_2O$, $CHCl_3$ and ether, and dried, in vacuo to give 0.185 g (53%) of compound 247 which was shown to be homogeneous by thin layer chromatography (BuOH:pyridine:AcOH:$H_2O$, 30:10:3:12, $R_f$=0.55), mp #175°-176.5° C.

6-[2'-(4''-Imidazolyl)ethylamino]heptanoic Acid p-Toluide (246)

Histamine dihydrochloride (0.18 g, 1.0 mmol), 6-oxoheptanoic acid p-toluide (0.23 g, 1.0 mmol) and sodium cyanoborohydride (0.06 g, 1.0 mmol) were dissolved in 5 ml MeOH in a vial that had been flushed with nitrogen. The reaction mixture was heated overnight at 55° C. To quench unreacted borohydride, 3 N HCl was added to pH 1-2 (pH paper). After the evolution of gas had subsided, the reaction mixture was added to 50 ml 0.1 N HCl and the solution extracted with $CHCl_3$. The aqueous phase was made basic by the addition of 20 ml 1 N NaOH and extracted with $CHCl_3$. The combined $CHCl_3$ fractions were back-extracted with brine and dried over $K_2CO_3$. Filtration to remove drying agent and removal of the solvent under reduced pressure gave the product as a clear glass. To convert the material to the dihydrochloride salt, the residue was redissolved in a small amount of $CHCl_3$ and 0.5 ml N HCl in dioxane was added dropwise. Removal of the solvents under reduced pressure followed by precipitation of the product from EtOH/ether gave 41 mg (10%) of compound 246 shown to be pure by thin layer chromatography (BuOH:pyridine:AcOH:H$_2$O, 30:10:3:12, R$_f$=0.35), mp 152°–155° C.

Methyl Branched Histamine Conjugates

The methyl branched N-alkylated histamine conjugates were synthesized via reductive amination from histamine dihydrochloride and the appropriate methyl ketone. This procedure is illustrated by the synthesis of 6-[2'-(4''-imidazolyl)ethylamino]heptanoic acid p-toluide (246). The syntheses of the methyl ketones are well known in the art. Table 1 lists reaction conditions and yields for the members of this series.

FCS, 2mM glutamine, 10% CAS and 5×10$^{-5}$M 2-mercaptoethanol and were later cloned by limiting dilution. The clones were maintained in RPMI 1640 medium with 10% PCS and 10% CAS.

NS cells were centrifuged and resuspended at b 1×10$^6$/ml in PBS and incubated at 37° C. for 10 min with 10mM IBMX at a final concentration at 20 µM. Alternatively the cells were resuspended in 5 mM HEPES and 1 mM MgSO$_4$ and after five minutes were disrupted in a Dounce homogenizer. Broken cells were centrifuged at 20,000 g (approximately 1,800 rpm) for thirty minutes and supernatant was discarded. The pel-

TABLE 1

Reaction Conditions for the Reductive Amination of Histamine and Methyl Ketones

| Compound | x in CH$_3$—C(=O)—(CH$_2$)$_n$-x | n | g (mmol) | Histamine Dihydrochloride g (mmol) | NaBH$_3$CN mg (mmol) | Solvent Volume ml | Reaction Time hr | Yield$^a$ Crude/Pure | TLC$^b$ R$_f$(solvent) |
|---|---|---|---|---|---|---|---|---|---|
| 246 (7) | —CONH-phi-p-CH$_3$ | 4 | 0.23 (1.0) | 0.18 (1.0) | 60 (1.0) | 5 | 48 | /10 | 0.35 (A) |
| 262 (8) | " | 5 | 0.25 (1.0) | 0.18 (1.0) | 60 (1.0) | 3 | 12 | 73/50 | 0.41 (A) 0.56 (B) |
| 263 (11) | —CONH-phi-o-CH$_3$ | 4 | 0.14 (0.50) | 0.092 (0.50) | 30 (0.50) | 3 | 12 | 68/47 | 0.38 (A) 0.59 (B) |
| 264 (6) | —CONH-phi-p-CH$_3$ | 3 | 0.11 (0.50) | 0.092 (0.50) | 31 (0.50) | 3 | 12 | 70/27 | 0.42 (A) |
| 265 (9) | —CONH-phi-p-CF$_3$ | 4 | 0.29 (1.0) | 0.18 (1.0) | 60 (1.0) | 3 | 12 | 63/37 | 0.42 (A) 0.54 (B) |
| 266 (12) | Boc-L-Phe—Gly—NHCH$_3$ \| NHCO— | 4 | 0.24 (0.50) | 0.092 (0.50) | 63 (1.1) | 5 | 12 | 80/30 | 0.30 (A) 0.47 (B) |
| 267 (13) | —CONH(CH$_2$)$_3$CH$_3$ | 4 | 0.54 (2.7) | 0.50 (2.7) | 340 (5.4) | 15 | 48$^c$ | /51 | 0.32 (A) 0.48 (B) |
| 268 (2) | —CH$_3$ | 4 | 0.31 (2.7) | 0.50 (2.7) | 340 (5.4) | 15 | 48$^c$ | /66 | 0.43 (A) 0.62 (B) |
| 299 (10) | —CONH-p-phi-CF$_3$ | 3 | 1.50 (5.5) | 1.05 (5.5) | 700 (11.0) | 40 | 24 | /20 | |

TABLE 2

Microchemical Analysis of Representative Histamine Congener Derivatives

| Compound | Formula | Formula Wt. | Calcd. C | Calcd. H | Calcd. N | Found C | Found H | Found N |
|---|---|---|---|---|---|---|---|---|
| 245 (3) | C$_{11}$H$_{19}$N$_3$O | 209.33 | 63.11 | 9.17 | 20.08 | 63.20 | 9.22 | 19.97 |
| 246 (7) | C$_{19}$H$_{30}$N$_4$OCl$_2$.1H$_2$O | 419.45 | 54.40 | 7.70 | 13.36 | 54.44 | 7.44 | 13.19 |
| 247 (4) | C$_{17}$H$_{22}$N$_4$O$_2$.1.5H$_2$O | 341.46 | 59.79 | 7.39 | 16.41 | 60.22 | 7.20 | 16.62 |
| 248 (1) | C$_{11}$H$_{23}$N$_3$Cl$_2$ | 268.26 | 49.25 | 8.66 | 15.67 | 48.90 | 8.84 | 15.42 |
| 249 (5) | C$_{17}$H$_{26}$N$_4$OCl$_2$ | 373.37 | 54.68 | 7.03 | 15.01 | 54.48 | 6.99 | 15.16 |
| 262 (8) | C$_{20}$H$_{32}$N$_4$OCl$_2$ | 415.46 | 57.82 | 7.78 | 13.49 | 57.69 | 7.57 | 13.39 |
| 263 (11) | C$_{19}$H$_{27}$N$_4$OCl$_2$F$_3$.0.5H$_2$O | 464.41 | 49.14 | 6.09 | 12.07 | 49.28 | 6.06 | 11.95 |
| 265 (9) | C$_{19}$H$_{27}$N$_4$OCl$_2$F$_3$.1H$_2$O | 473.42 | 48.20 | 6.19 | 11.84 | 48.22 | 6.34 | 11.78 |
| 267 (13) | C$_{16}$H$_{32}$N$_4$OCl$_2$ | 367.41 | 52.30 | 8.80 | 15.25 | 51.89 | 8.36 | 15.00 |
| 268 (2) | C$_{12}$H$_{25}$N$_3$Cl$_2$ | 282.29 | 51.05 | 8.94 | 14.89 | 50.71 | 8.55 | 14.73 |
| 299 (10) | C$_{18}$H$_{25}$N$_4$OCl$_2$F$_3$.5H$_2$O | 450.33 | 48.01 | 5.82 | 12.44 | 47.35 | 5.69 | 12.09 |

EXAMPLE II Determination of Biological Activity Natural Suppressor Cells and the Assay of their cAMP NS cells were obtained and cultured as follows: four- to six-month old BALB/c mice were anesthetized with pentobarbital and all major lymphoid organs, including all major lymph nodes, the spleen, and the thymus, were irradiated as described by Slavin et al., Science (1976) 193:1252. The skull, lungs, and hind legs were shielded with lead. The mice were given 200 rad per day, 5 times per week, to a total dose of 3400 rad. Irradiation was delivered from a single 250 kV (15A) source (Philips Medical Systems, Inc., Shelton, CT). The mice were killed between 5 and 15 days after completion of the TLI. Spleens were removed aseptically and single cell suspensions were prepared by gently pressing the spleen fragments through a nylon fiber mesh (Tetko, Inc., Elmsford, NY). These spleen cells were fed daily with tissue culture medium containing RPMI 1640, 10% let was resuspended in Tris (pH 7.5), 5 mM HEPES and 1 mM MgSO$_4$ and incubated with IBMX.

The cells were incubated with and without histamine derivatives for 1 min.at 37° C. with continuous shaking. Maximum intracellular accumulation of cAMP occurred in one minute. Cold TCA (100%) was added to a final concentration of 8% and the tubes were stored in ice. Samples were extracted 3 times with 3 volumes of ether. The ether was evaporated at 40° C. in a water bath for approximately 45 min. Acetylation of both experimental samples and cAMP standards were performed by addition of 10µl of a mixture of triethylamine and acetic anhydride (2:1). Acetylation improved the sensitivity of the assay about 50- to 100-fold. The radioimmunoassay was performed as reported previously by Khan et al., *J. Clin. Invest.* (1985) 75:1578.

Guinea pig myocardial adenylate cyclase assay

Male, partly albino, guinea pigs (600 g average weight) were killed by a blow to the head. The hearts were excised and immediately immersed in ice cold oxygenated Tyrode's solution. Both ventricles were dissected free and placed in 250 mM sucrose, 5 mM Tris, 1 mM EDTA, pH 7.45. The tissue was minced with a screen, and was then homogenized with 3 consecutive 5 sec bursts of a Polytron (Brinkman Instruments, Inc., Westbury, NY) at a setting of 11. The homogenate was then centrifuged at $1085 \times g$ for 20 min. The pellet was resuspended and recentrifuged twice. The final suspension was filtered through four layers of gauze. Adenylate cyclase was assayed by the method of Salomon et al., *Anal. Biochem.* (1974) 58:541 as modified by Bristow et al., *Mol Pharmacol.* (1982) 21:671. Enzyme protein (75–250µg) was added to a reaction mixture that consisted of 0.1 mM Mg ATP, 0.5 mM $MgCl_2$, 10 mM phosphocreatine, 14.5 µg of creatine kinase (1381 U/mg), 100mM 7.45), $10^{-5}$M guanylimidophosphate (GPP(NH)P) and variable concentrations of histamine. $^3H$ labelled cyclic AMP (10,000–12,000 cpm/assay) was added prior to incubation for determination of recovery. The final reaction volume before addition of $[\alpha\text{-}^{32}P]ATP$ was 225 µl. Reaction tubes were stored in cryogenic racks (Kryorack, Isolab, Inc. Akron, OH) at 0° C.

The reaction mixture was pre-warmed in a shaking water bath at 30° C. for 5 min after which 25µl (1.25–2.5Ci) of $[\alpha\text{-}^{32}P]ATP$ (250–500 Ci/mM) was added to label the ATP pool. The assay time was 20 min, the time needed for measurable stimulation of adenylate cyclase. The $^{32}P$ reaction was stopped by the addition of 750 µl of 1% sodium dodecysulfate. $^{32}P$-labelled cyclic AMP was then isolated by the dual Dowex-alumina column method of Salomon et al., supra. $[\alpha\text{-}^{32}P]ATP$ (New England Nuclear Corporation, Boston, MA) that gave reagent blanks of 50 cpm was purified on Dowex columns as described by Salomon et al., supra. Recovery of cAMP ranged from 70 to 90%. Reagent blanks exhibited 0.005% of the activity of the added $[\alpha\text{-}^{32}P]ATP$ and were in all cases less than 10% of basal activity. All assays were performed in duplicate and activity was linear with respect to added enzyme protein and to time over a period of 5–30 min. The coefficient of variability of the duplicates was less than 5%.

Blocking histamine effects in natural suppressor cells

This assay was carried out in the same fashion as already described for the derivatives except that ED-90 concentration of the test compound was chosen. Cimetidine was added at the same time in concentrations ranging from $10^{-4}$ to $10^{-8}$M. Alternatively, $10^{-6}$M cimetidine was added to $10^{-3}$–$10^{-8}$M concentration of agonists.

Mixed leukocyte reaction (MLR) suppressor assay

Responder (BALB/c) and stimulator (C57 BL/6) spleen cells ($5 \times 10^5$ each) were incubated with graded numbers of NS cells in 0.3 ml/well in 96-well flat bottomed microculture plates (Costar, Data Packaging, Cambridge, MA). The culture medium was supplemented with 100 U/ml penicillin, 100 ug/ml of streptomycin (both GIBCO, Grand Island, NY), and 10 =pooled human serum (VSP human serum, Biocell Laboratories, Carson CA). Co-cultured cells and stimulator cells were given 3300 rad before incubation. Cultures were maintained at 37° C. in 5% CO2 for 5 or 6 days. Eighteen hr before termination, 1µCi of $[^3H]$-thymidine (specific activity 6.7 Ci/ml) (New England Nuclear, Boston, MA) was added to each culture. Cells were harvested as described above. The data were expressed as the arithmetic mean of triplicate cultures. Suppression was calculated as follows: percent suppression = 1 − (CPM with co-cultured cells)/(CPM without co-cultured cells) × 100. To test the activation capability of congener derivatives of histamine, the natural suppressor cells were incubated with agonist ($10^{-4}$M) for 4 hr at 37° C. and washed 3 times before the cells were co-cultured in an MLR. To block the effects of agonists, $10^5$M cimetidine was used as an $H_2$ antagonist and $10^{-6}$M mepyramine was used as an $H_1$ antagonist. The results are set forth in Table 3.

Dose-response characteristics of histamine-mediated adenylate-cyclase stimulation in natural suppressor cells In the presence of IBMX, histamine stimulated cAMP from 2- to 6-fold over the basal levels. Basal cAMP levels in lymphoid cells ranged from 0.2 to 1 pmole/$1 \times 10^6$ cells. An EC-50 value of $3 \times 10^{-5}$M $\pm 4.3 \times 10^{-6}$ was calculated from at least six concentrations of histamine in duplicates or triplicates.

Dimaprit (EC-50 $6 \times 10^{-5}$M) (dimaprit, an $H_2$ receptor agonist, was supplied by Smith Kline and French, Welwyn Garden City, Hertfordshire, England) had $H_2$ effects on the NS cells but did not produce the same maximal effects as histamine on cAMP concentrations.

Effect of beta adrenergic blockade

Because histamine may release catecholamines in certain preparations, the effect histamine on cAMP accumulation in lymphoid cells in the presence of $6 \times 10^{-6}$M propranolol was evaluated. lol had no effect on histamine-induced intracel accumulation of cAMP in lymphoid cells. In these cells $6 \times 10^{-6}$M propranolol completely blocked the effects of $10^{-5}$M isoproterenol.

Blockade by $H_2$ antagonists

Dose response curves for histamine and dimaprit were determined from $10^{-3}$M to $10^{-8}$M in the presence or absence of $10^{-6}$M cimetidine. This concentration of cimetidine did not lower the basal activity. The dose response curves for histamine and dimaprit exhibited parallel shifts to the right following treatment with the $H_2$ antagonist cimetidine. The inhibition constant calculated for cimetidine was 0.11–0.43µM in lymphoid cells.

The effects of histamine derivatives on cAMP accumulation in natural suppressor cells The derivatives of histamine had a wide spectrum of pharmacologic activity on NS cells. These effects were not unique for a given clone or parental NS cell line. At least four different clones and two different parent lines produced similar EC-50 values for the derivatives tested (Table 3). While none of the derivatives of histamine was equally efficacious as histamine some were more potent than histamine. The manipulation of structure far removed from the imidazole moiety (i.e., the histamine receptor recognition site) did not result in loss of the histaminelike activity in most of the derivatives. Simple alkylation of the primary amino group resulted in a derivative containing an unbranched alkyl side chain (compound 1) which was about equipotent to histamine. Both the methyl-branched alkylated analog (compound 2) and the acylated analog (compound 3) were inactive (Table 3).

When the terminal methyl group in an inactive methyl-branched derivative (compound 2) was replaced by a toluide moiety, the resulting derivative (compound 7) was three times as potent as histamine. Similarly, modification of an inactive acylated derivative (compound 3) to produce a toluide derivative of approximately the same chain length (compound 4) resulted in an analog which was four times more potent than histamine. When a carbonyl group of the latter acylated compound was replaced by a two carbon unit resulting in an alkylated derivative containing a methyl-branched alkyl spacer group (compound 6), the activity was 3000 fold greater than histamine.

In general the potency of compounds 6, 7 and 8 was also dependent upon the length of the alkyl spacer group. Thus, compounds 6, 7 and 8, had widely divergent activity: as the methyl chain lengthened, the potency fell.

Substituents on the aromatic ring also were determinants of the activity of the toluide derivatives. When a para-methyl substituent (compound 7) was replaced by a more electron-withdrawing trifluoromethyl group, the resulting derivative (compound 9) lost a significant amount of maximal efficacy but was 40,000-fold more potent than histamine. Compound 9 was the most potent of this series on H2 receptors. When compound 9 was further modified by changing the methylene chain length to 3, the compound lost all of its activity as an $H_2$ agonist but became a pure $H_1$ agonist when measured in the MLR assay. Furthermore, a shift of the trifluoromethyl group from the para to ortho position (compound 11) dramatically nullified both detectable $H_1$ and $H_2$ activity (Tables 3 and 5).

Neither an aliphatic amide derivative of histamine (compound 3) nor the dipeptide conjugate of histamine (compound 12) altered intracellular cAMP in the NS cells.

Compounds 2, 3, 11, 12, and 13, which were impotent as H2 receptor agonists on NS cells, also failed to block histamine mediated accumulation of cAMP in NS cells, suggesting that none of these compounds was a histamine ($H_2$) receptor antagonist. Some of the histamine derivatives were also tested for their efficacy and potency in broken membrane preparations of lymphoid cells. The derived EC-50 values were not significantly different ($<0.05$, N TM 4) in whole cells versus broken membrane preparations.

Potencies of test compounds on guinea pig myocardial adenylate cyclase

In preparations from guinea pig myocardium, histamine caused a 3- to 5-fold stimulation of basal adenylate cyclase activity. Activity was linear with time for at least 20 min following the addition of [$\alpha$-$^{32}$P]ATP. All of the derivatives were strikingly less potent and had much lower maximal efficacy than histamine in this assay. The relative potencies for compounds 6, 9, and 13 are shown in Table 4. While derivatives 6 and 9 were very potent in NS cell cAMP assays (Table 3), they were strikingly impotent in guinea pig myocardium (Table 4) thus illustrating the tissue and effect specificity of the derivatives.

As shown in Table 4, branched or unbranched alkylated derivatives (compounds 1 and 2) or acylated derivatives (compound 3) of the primary amino group on histamine were completely inactive on the isolated guinea pig heart. Furthermore, the acylated histamine analog which contained a toluide moiety (compound 4) that had been very active on NS cells was inactive on the guinea pig myocardium. However, addition of the toluide group to either a branched or an unbranched alkylated analog (compounds 5-8) produced histamine-like activity on the myocardium. Once again the relative potency of compounds 6, 7 and 8 followed the same rank order of potency found in the NS cells. It was most interesting that replacement of the paramethyl group by the electronegative trifluoromethyl group in either the para or ortho position resulted in inactive compounds, further illustrating the tissue specificity created by the changes in the structure of the molecule.

The tissue selective potency of compounds 6 and 9 was most striking and potentially useful. Compound 6 was three orders of magnitude more potent than histamine on NS cells but less potent than histamine on the myocardium. Similarly compound 9 was 4 orders of magnitude more potent than histamine on the NS cells but did not stimulate adenylate cyclase in guinea pig myocardium. Compound 10 was found to produce only $H_1$ agonistic action.

Tissue selective responsiveness was further illustrated by the histamine peptide conjugate (compound 12) and the aliphatic derivative (compound 13) which were inactive on NS cells but stimulated guinea pig myocardium. The data show that histamine derivatives have selective action in vitro for guinea pig myocardium versus murine lymphoid cells.

Blocking the effects of derivatives of histamine on lymphoid cells

Cimetidine, an $H_2$ antagonist, was used as an antagonist of cAMP accumulation by the subject compounds on the NS cells. The data show that, with the exception of compounds 1 and 4, all derivatives of histamine were competitively antagonized by the $H_2$ antagonist. Cimetidine at $10^{-5}$M competitively blocked the actions of compounds 6-8 (used at $10^{-4}$M) and 9 (used at $10^{-7}$M) on the intracellular accumulation of cAMP in the NS cells. The effects of compounds 6 and 9 could not be completely inhibited by the $H_2$ antagonist; the other compounds were completely inhibited.

The activities of compounds 1 and 4, which had little or no effect on the myocardium but were equipotent to histamine on the lymphocyte accumulation of cyclic AMP were not inhibited by the $H_2$ antagonist. Compounds 6 and 8 have very weak effects and compound 10 had no effect on the guinea pig myocardium which, presumably, exclusively expresses $H_2$ receptors. See, Johnson et al., *Mol. Pharmacol.* (1979) 16:417.

Increased suppressor activity of natural suppressor (NS) cells produced by derivatives of histamine In order to study the effect of derivatives of histamine on the biologic suppressor activity of the cells, one established clone (C-8) was incubated in 10% CAS, 10% FCS and RPMI 1640 medium containing $10^{-4}$M derivatives of histamine for four hours before washing the cells and adding the to responder and stimulator cells. Co-cultured and stimulator cells were given 3300 rad in vitro just prior to incubation. It has been reported that under such conditions histamine augmented the suppressive capacity of NS cells via $H_1$ receptors. See, Khan et al., *J. Immunol.* (1985) 134:4100. Table 5 shows the activity of various derivatives. The drug augmented suppression of MLR by NS cells. To determine the role of $H_1$ and $H_2$ receptors in the modification of NS cell function, the incubation with compound 10 was carried out in the presence of either cimetidine ($10^{-5}$M) or mepyramine ($10^{-6}$M) for four hours at 37° C. The cells were then washed extensively and later added to co-cultures with responder and stimulator cells. The $H_1$ antagonist, mepyramine, reversed the increase in suppressive activity of the derivative-stimulated NS cells. However, the $H_2$ antagonist, cimetidine, did not alter the derivative-enhanced suppression. Similar experiments were carried out with each of the indicated agonists (Table 5). All of the compounds that augmented NS function did so by $H_1$ action.

As shown in Table 5, compounds 2, 3, and 13 had no $H_1$ activity, nor did they stimulate intracellular accumulation of cAMP that was mediated by $H_2$ receptors. However, compounds 6 and 9 retained $H_2$ activity as shown in Table 3, but compound 10 lost all $H_2$ activity and appeared to be a specific $H_1$ receptor agonist.

TABLE 3

Activity of Histamine Congener Derivatives on Natural Suppressor Cells

| COMPOUND | RELATIVE POTENCY | EC$_{50}$ |
| --- | --- | --- |
| Histamine | 1.0 | $1.8 \times 10^{-5} \pm 4.3 \times 10^{-6}$ |
| 1 | $0.5 \times 10^1$ | $3.2 \times 10^{-6} \pm 7.0 \times 10^{-8}$ |
| 2 | Inactive | |
| 3 | Inactive | |
| 4 | $0.4 \times 10^1$ | $4.4 \times 10^{-6} \pm 6.0 \times 10^{-8}$ |
| 5 | $0.2 \times 10^1$ | $7.5 \times 10^{-6} \pm 1.6 \times 10^{-6}$ |
| 6* | $3.8 \times 10^3$ | $4.6 \times 10^{-9} \pm 1.13 \times 10^{-9}$ |
| 7 | $0.3 \times 10^1$ | $6.2 \times 10^{-6} \pm 2.2 \times 10^{-6}$ |
| 8 | $0.2 \times 10^1$ | $8.7 \times 10^{-6} \pm 2.6 \times 10^{-6}$ |
| 9* | $4.3 \times 10^4$ | $4.1 \times 10^{-10} \pm 2.12 \times 10^{-11}$ |
| 10 | Inactive | |
| 11 | Inactive | |
| 12 | Inactive | |
| 13 | Inactive | |

*Dose response curve and relative potency were signficantly different from histamine and compounds 1, 4 and 5 ($P < 0.05$, $N = 3 - 6$).

TABLE 4

Activity of Histamine Congener Derivatives On Guinea Pig Myocardium

| COMPOUND | RELATIVE POTENCY | EC$_{50}$ |
| --- | --- | --- |
| Histamine | 1.0 | $1.7 \times 10^{-7}$ |
| 1 | Inactive | |
| 2 | Inactive | |
| 3 | Inactive | |
| 4 | Inactive | |
| 5 | $0.9 \times 10^{-1}$ | $1.9 \times 10^{-6}$ |
| 6 | $0.1 \times 10^{-1}$ | $1.4 \times 10^{-5}$ |
| 7 | $0.7 \times 10^{-1}$ | $2.2 \times 10^{-6}$ |
| 8 | $0.2 \times 10^{-1}$ | $5.8 \times 10^{-6}$ |
| 9 | Inactive | |
| 10 | Inactive | |
| 11 | Inactive | |
| 12 | $0.7 \times 10^{-3}$ | $2.3 \times 10^{-4}$ |
| 13 | $0.1 \times 10^{-1}$ | $1.3 \times 10^{-5}$ |

Interaction of histamine ($10^{-5}$M) with the receptors resulted in three-fold stimulation of adenylate cyclase over base levels. The EC$_{50}$ value is an average of duplicates calculated from at least six concentrations of agonists with SEM < 5%. Congenes 5 and 6 were significantly different in their activity ($P < 0.005$) when compared with histamine.

TABLE 5

Induction of Natural Suppressor Cell Activity In MLR By Congener Derivatives Of Histamine

| Compound | % Suppression By NS Cells in MLR | % Suppression by NS* Cells In MLR After Treatment With Congener | p** |
| --- | --- | --- | --- |
| Histamine | 44 ± 4 | 60 ± 2 | <.01 |
| 1 | 50 ± 3 | 66 ± 4 | <.01 |
| 2 | 40 ± 4 | 41 ± 3 | >.05 |
| 3 | 66 ± 2 | 64 ± 5 | >.05 |
| 5 | 41 ± 3 | 56 ± 5 | <.01 |
| 6 | 42 ± 3 | 54 ± 2 | <.01 |
| 7 | 49 ± 4 | 56 ± 4 | >.05 |
| 8 | 54 ± 3 | 73 ± 6 | <.01 |
| 9 | 46 ± 1 | 65 ± 1 | <.001 |
| 10 | 48 ± 6 | 74 ± 1 | <.01 |
| 11 | 55 ± 5 | 57 ± 1 | >.05 |
| 13 | 51 ± 4 | 56 ± 5 | >.05 |

*TLI - 2 - C8 cells ($5 \times 10^3$) were preincubated with the agonists for four hours before being extensively washed and added to the MLR. Percent suppression ± SEM ($N = 3 - 5$) is compared to control MLR without co-cultured cells.
**P values were calculated by using the student t-test to compare the results from three to five independent determinations.

The subject compounds find wide use as agonists or antagonists for $H_1$ and/or $H_2$ receptors of lymphocytes, moderating various physiological activities in accordance with the effect resulting from binding of the histamine derivatives to the receptor. Thus, specific or nonspecific effects can be achieved depending upon the derivative employed. In some situations, mixtures of derivatives may be employed to vary the desired effect.

Although the foregoing invention has been described in some detail by way of illustration and example for purposes of clarity of understanding, it will be obvious that certain changes and modifications may be practiced within the scope of the appended claims.

What is claimed is:

1. Histamine derivatives having binding specificity for $H_1$ or $H_2$ receptors of lymphocytes being characterized by being mono-substituted at the side chain amine of a histamine molecule with a substituent having an aliphatic chain of from 2 to 10 carbon atoms, wherein the alpha-carbon of the chain is substituted with oxo or alkyl of from 1 to 3 carbon atoms, said chain terminating in hydrogen or carboxamido, wherein the carboxamido nitrogen is substituted with alkyl of from 1 to 6 carbon atoms, tolyl, or trifluoromethylphenyl, with the proviso that when said chain terminates in hydrogen, the chain length is 5 or 6 atoms.

2. Histamine derivatives according to claim 1, wherein said alpha-carbon is substituted with methyl and said aliphatic chain is polymethylene.

3. Histamine derivatives according to claim 1, wherein said carboxamido nitrogen is substituted with tolyl or trifluoromethylphenyl.

4. Histamine derivatives having binding specificity for $H_1$ or $H_2$ receptors of lymphocytes and of the formula

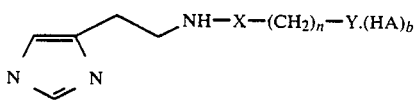

wherein:
X is CO or CHR, where R is an alkyl group of from 1 to 3 carbon atoms;
n is an integer of from 2 to 6;

Y is $CH_3$ or CONHZ, wherein Z is H; $(CH_2)_mCH_3$, where m is 1 to 4; substituted phenyl, where the substituent is methyl or trifluoromethyl;

A is a physiologically acceptable counterion; and b is an integer of from 0 to 2.

5. Histamine derivatives according to claim 4, wherein Y is $CH_3$.

6. Histamine derivatives according to claim 4, wherein Y is (CO)NHZ.

7. Histamine derivatives according to claim 6, wherein Z is substituted phenyl, where the substituent is methyl or trifluoromethyl.

8. Histamine derivatives according to claim 4, wherein b is 0.

9. Histamine derivatives having binding specificity for $H_1$ or $H_2$ receptors of lymphocytes and of the formula

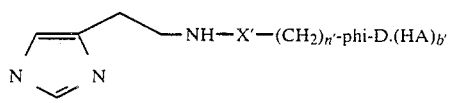

wherein:

n' is 2 to 5;

X' is CO, $CH_2$, or $CHCH_3$;

D is methyl or trifluoromethyl;

phi is phenylene;

A is a physiologically acceptable counterion; and b' is an integer of from 0 to 2.

10. Histamine derivatives having binding specificity for $H_1$ or $H_2$ receptors of lymphocytes and of the formula

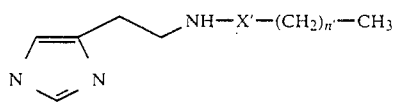

wherein:

X' is CO, $CH_2$, or $CHCH_3$; and n' is 2 or 3.

11. A method of modulating an immune response of lymphocytes, which comprises contacting said lymphocytes with an immunomodulating amount of a compound according to claim 1.

12. A method of modulating an immune response of lymphocytes, which comprises contacting said lymphocytes with an immunomodulating amount of a compound according to claim 2.

13. A method of modulating an immune response of lymphocytes, which comprises contacting said lymphocytes with an immunomodulating amount of a compound according to claim 4.

14. A formulating comprising a histamine derivative according to claim 1 in a physiologically acceptable carrier.

15. A formulation comprising a histamine derivative according to claim 2 in a physiologically acceptable carrier.

16. A formulation comprising at least 2 histamine derivatives according to claim 1 in a physiologically acceptable carrier.

* * * * *